US00PP18553P2

(12) United States Plant Patent
Zary

(10) Patent No.: US PP18,553 P2
(45) Date of Patent: Mar. 4, 2008

(54) HYBRID TEA ROSE PLANT NAMED 'JACPRIBE'

(50) Latin Name: *Rosa hybrida*
Varietal Denomination: JACpribe

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/586,184

(22) Filed: Oct. 24, 2006

(51) Int. Cl.
*A01H 5/00* (2006.01)

(52) U.S. Cl. ..... Plt./139

(58) Field of Classification Search ..... Plt./139
See application file for complete search history.

(56) References Cited

U.S. PATENT DOCUMENTS

PP3,997 P * 12/1976 Warriner ..... Plt./132
PP6,264 P * 8/1988 Olesen et al. ..... Plt./139
PP8,591 P * 2/1994 Warriner ..... Plt./132

* cited by examiner

*Primary Examiner*—Wendy Haas
(74) *Attorney, Agent, or Firm*—Klarquist Sparkman LLP

(57) ABSTRACT

Hybrid tea rose plant having vigorous, but compact growth habit; large, well-formed flowers borne one per stem; thick petals; leathery foliage; and good disease resistance.

1 Drawing Sheet

Figure 1:
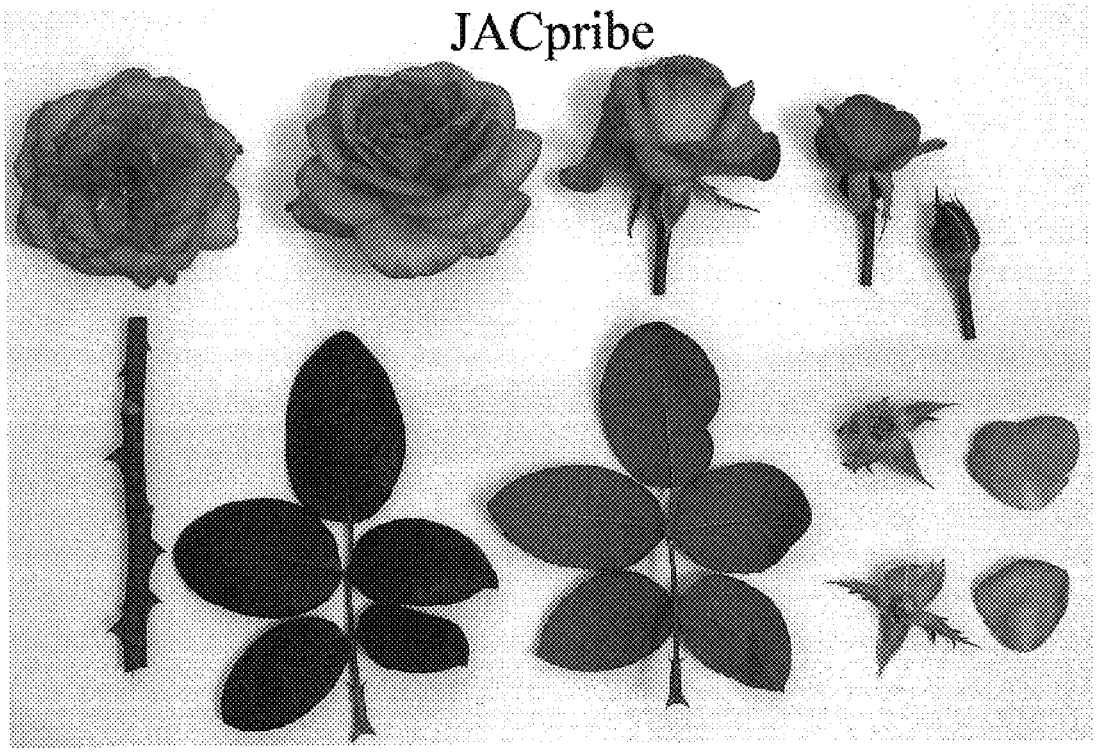

Genus and species: *Rosa* hybrid.
Variety denomination: 'JACpribe'.

ORIGIN OF THE INVENTION

The present invention relates to a new and distinct variety of a hybrid tea rose plant named 'JACpribe' which was originated by me by crossing the variety 'POULman' (U.S. Plant Pat. No. 6,264) with the variety 'JACpico' (U.S. Plant Pat. 3,997).

BACKGROUND OF THE INVENTION

The primary objective of this breeding was to produce a new rose variety having a compact plant, strong leathery foliage and the disease tolerance of the female parent combined with the high centered flower form and thick petals of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous, but compact growth habit.
2. Large, well-formed flowers borne one per stem.
3. Thick petals.
4. Leathery foliage.
5. Good disease resistance.

Asexual reproduction of this new variety by cuttings, as performed at Wasco and Somis, Calif., shows that the foregoing and all other characteristics and distinctions come true to form and are established and transmitted through succeeding propagations.

COMPARISON WITH PARENTS

'POULman', the female parent, is a red hybrid tea with flowers on stems of 30 to 45 cm. It is resistant to powdery mildew and rust and very tolerant to blackspot. The male parent, 'JACpico', is also a hybrid tea but with white flowers having a pink blush on 40 to 50 cm stems. It is resistant to powdery mildew and rust but susceptible to blackspot.

COMPARISON WITH SIMILAR VARIETY

'JACpribe' is a very compact hybrid, ideal for containers. Well formed flowers are produced singly on short stems. This combined with good disease tolerance makes it a unique variety. It differs from 'JACpal' (U.S. Plant Pat. No. 8,591) in having shorter stems, a more compact plant and improved disease resistance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Ingrid Bergman 'POULman', (U.S. Plant Pat. No. 6,264).

*Pollen parent.*—Pristine 'JACpico', (U.S. Plant Pat. No. 3,997).

FLOWER

Observations made from January 2005 to July 2006 from plants commencing at three years of age grown in a garden environment at Somis, Calif.

Blooming habit: Continuous.

Bud:

*Size.*—About 45 mm long and 35 mm in diameter when the petals start to unfurl.

*Form.*—The bud form is long, pointed ovoid.

*Color.*—When sepals first divide, bud color is Red Group 43C. When half blown, the upper sides of the petals are Red Group 43C and the lower sides of the petals are Red Group 48C.

*Sepals.*—Color: Upper surface: Green Group N138C. Lower surface: Yellow-Green Group 146C, often with an overlay of Greyed-Red Group 178C when exposed to sunlight. Length: 27–30 mm. Width: 8–9 mm. Shape: Acuminate. Surface texture: Hoary. There are three lightly to normally appendaged sepals. There are two unappendaged sepals with hairy edges.

*Receptacle.*—Color: Yellow-Green Group 146C. Shape: Funnel. Size: Medium, about 8–9 mm wide× 4–5 mm long. Surface: Smooth.

*Peduncle.*—Length: Short, averaging about 6–7 cm. Surface: Smooth, with an occasional gland. Color: Yellow-Green Group 146C, often with an overlay of Greyed-Red Group 178C when exposed to sunlight. Strength: Stiff, erect.

Bloom:

*Size.*—Medium. Average open diameter is about 10–11 cm.

*Borne.*—Singly.

*Stems.*—Strength: Strong. Average length is about 30 cm with a diameter of 7–8 mm.

*Form.*—When first open: High centered. Permanence: Outer petals curl back, quill fashion.

*Petalage.*—Number of petals under normal conditions: 30–35.

*Color.*—The upper sides of the petals are Red Group 43C. The reverse sides of the petals are Red Group 43D. The base of the petals has a small 4 mm×4 mm Yellow Group 12C color spot. The major color on the upper side is Red Group 43C.

*Variegations.*—None.

*Discoloration.*—The general tonality at the end of the first day: No change. At the end of the third day: No change. Further aging: By day 5 or 6 there is general fading to Red Group 48C and at petal drop to Red Group 48D.

*Fragrance.*—Moderate, spicy.

Petals:

*Texture.*—Thick, leathery.

*Shape.*—Smooth.

*Surface.*—Round to obcordate.

*Margin.*—Entire. Apex Shape: Obtuse to obcordate. Base Shape: Rounded.

*Form.*—Tips slightly recurved, edges slightly quilled.

*Arrangement.*—Imbricated.

*Petaloids.*—Number: 3 to 12. Size: 8–20 mm long× 5–16 mm wide. Color: Red Group 43B.

*Persistence.*—Petals drop off cleanly before drying.

*Lastingness.*—On the plant: Long (about 7–8 days). As a cut flower: Long (about 8–9 days).

Reproductive parts:

*Stamens.*—Number: 45–60. Length: 7–9 mm. Anthers: Length: 3 mm. Color: Yellow-Orange Group 16C. Filaments: Color: Red Group 46C. Length: 4–6 mm. Pollen: Color: Orange Group 26B.

*Pistils.*—Number: 40–45. Length: 6–7 mm. Styles: Color: Greyed-Purple Group 183D. Length: 5–6 mm. Stigmas: Color: Greyed-Purple Group 186D. Length: 1 mm.

*Hips.*—None observed, appears to be sterile.

PLANT

Form: Bush.

Growth: Vigorous, compact.

Age at maturity: One year.

Mature plant: Height: 4 ft. Width: 3 ft.

Rootstock: Own root.

Foliage: Number of leaflets on normal mid-stem leaves: 5 or 7.

*Size.*—Medium. About 15 cm long×10 cm wide.

*Quantity.*—Normal.

*Color.*—New foliage: Upper side: Greyed-Red Group 178A. Lower side: Greyed-Purple Group 183D. Old foliage: Upper side: Green Group 139A. Lower side: Green Group 137C.

Leaflets:

*Size.*—About 45–50 mm long×30–35 mm wide.

*Shape.*—Pointed oval.

*Base shape.*—Rounded.

*Apex shape.*—Acuminate.

*Texture.*—Leathery, glossy.

*Edge.*—Serrated.

*Serrations.*—Single, small.

*Petiole.*—Color: Green Group 137B.

*Petiole rachis.*—Color: Yellow-Green Group 148C. Underside: Rough with prickles.

*Auricles.*—None.

*Stipules.*—Length: 11–13 mm, serrated.

*Disease resistance.*—Resistant to rust and mildew and susceptible to blackspot under normal growing conditions.

*Pest resistance.*—Not observed.

*Vein color.*—Yellow-Green Group 148C.

*Venation pattern.*—Reticulate.

Wood:

*New wood.*—Color: Yellow-Green Group 146C, often with an overlay of Greyed-Purple Group 183C. Bark: Smooth.

*Old wood.*—Color: Green Group 137C. Bark: Smooth.

Prickles:

*Quantity.*—On main canes from base: Ordinary (8–10 per 15 cm of stem). On laterals from main canes: Ordinary (8–10 per 15 cm of stem).

*Form.*—Hooked slightly downward.

*Length.*—6–7 mm.

*Color when young.*—Greyed-Purple Group 183C.

*Color when Mature.*—Greyed-Orange Group 166D.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by its vigorous, but compact growth habit; large, well-formed flower borne one per stem; thick petals; leathery foliage; and good disease resistance.

* * * * *

UNITED STATES PATENT AND TRADEMARK OFFICE

CERTIFICATE OF CORRECTION

PATENT NO. : PP 18,553 P2
APPLICATION NO. : 11/586184
DATED : March 4, 2008
INVENTOR(S) : Keith Zary It is certified that error appears in the above-identified patent and that said Letters Patent is hereby corrected as shown below:

In the Specification:

Column 3, line 25, "widex 4-5 mm" should read -- wide x 4-5 mm --

Column 4, line 2, "45 60." should read -- 45-60. --

Column 4, line 4, "4 6 mm" should read -- 4-6 mm --

Signed and Sealed this

Sixth Day of April, 2010

David J. Kappos

David J. Kappos
*Director of the United States Patent and Trademark Office*